(12) United States Patent
Limousin

(10) Patent No.: US 6,711,441 B2
(45) Date of Patent: Mar. 23, 2004

(54) DETECTION OF FUSION IN AN ACTIVE IMPLANTABLE MEDICAL DEVICE, IN PARTICULAR A PACEMAKER, DEFIBRILLATOR OR CARDIOVERTOR

(75) Inventor: Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 10/021,803

(22) Filed: Dec. 12, 2001

(65) Prior Publication Data
US 2002/0095185 A1 Jul. 18, 2002

(30) Foreign Application Priority Data
Dec. 12, 2000 (FR) .............................. 00 16098

(51) Int. Cl.$^7$ ............................... A61N 1/362
(52) U.S. Cl. ........................... 607/28; 607/27
(58) Field of Search ...................... 607/28, 27

(56) References Cited

U.S. PATENT DOCUMENTS

| 4,969,464 A | 11/1990 | Callaghan et al. ..... 128/419 PG |
| 5,626,620 A | 5/1997 | Kieval et al. .................. 607/9 |
| 5,855,594 A | 1/1999 | Olive et al. .................... 607/28 |
| 6,456,881 B1 * | 9/2002 | Bornzin et al. ................ 607/27 |

FOREIGN PATENT DOCUMENTS

| WO | WO 93/02741 | 2/1993 | ............ A61N/1/36 |

* cited by examiner

Primary Examiner—George R. Evanisko
(74) Attorney, Agent, or Firm—Orrick, Herrington & Sutcliffe, LLP

(57) ABSTRACT

An active implantable medical device such as a pacemaker, defibrillator or cardioverter, able to detect a fusion situation for improving a capture threshold determination. This device is able to deliver to the patient's heart stimulation pulses presenting a predetermined amplitude and a duration, and adjusting the amplitude of these pulses. The adjustment involves calibrating the pulse amplitude, and delivering a stimulation pulse at null or at a primarily null voltage, and measuring automatically the ventricular capture threshold, including detecting the presence or absence of a capture consecutive to a stimulation. The fusion situation is monitored and, in the event of detected fusion situation, used to invalidate the adjustment of the stimulation pulse amplitude. This operates by delivering a stimulation pulse at null or primarily null voltage, and determining the presence of a fusion situation in the event of a detection of a capture in response to a stimulation at null or at primarily null voltage.

5 Claims, 2 Drawing Sheets

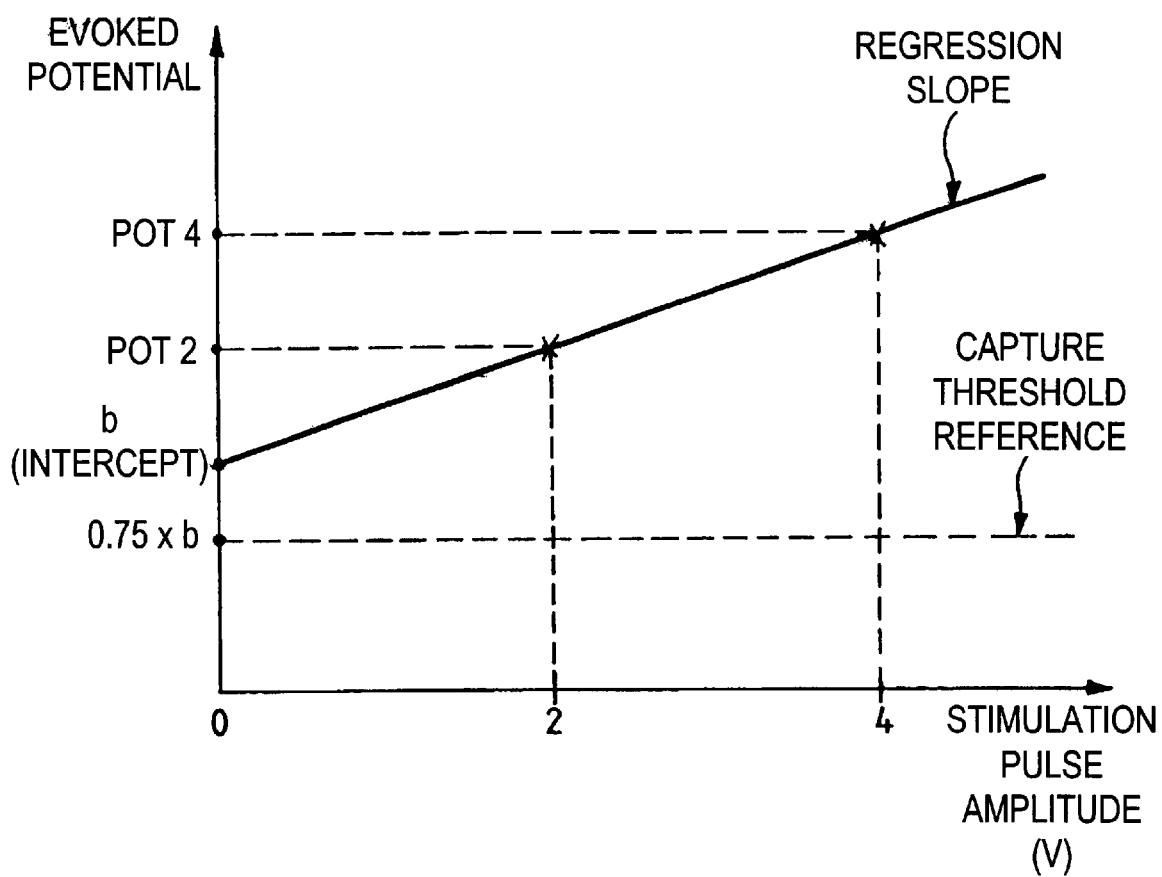
FIG_1

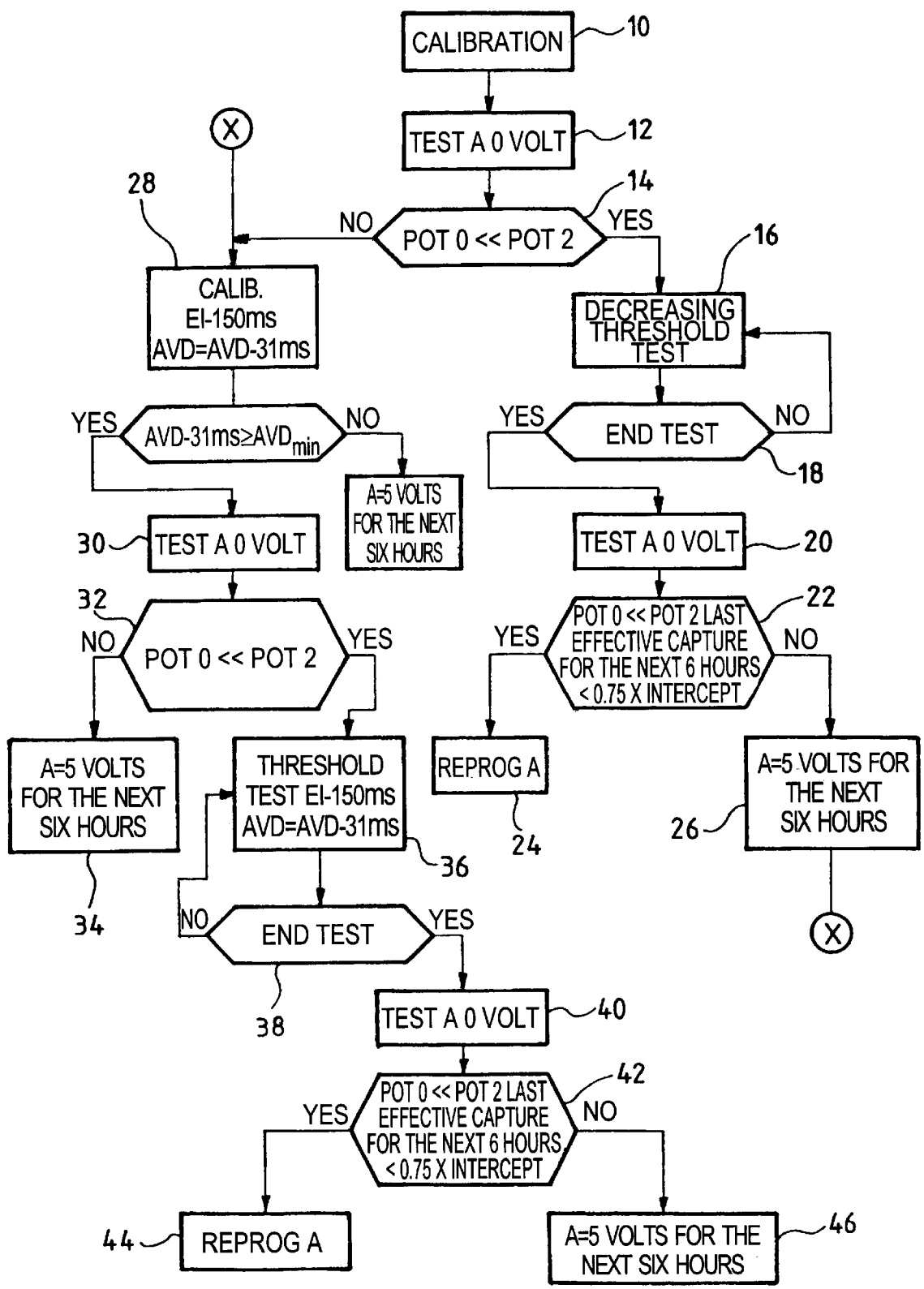

DETECTION OF FUSION IN AN ACTIVE IMPLANTABLE MEDICAL DEVICE, IN PARTICULAR A PACEMAKER, DEFIBRILLATOR OR CARDIOVERTOR

FIELD OF THE INVENTION

The present invention is directed to "active implantable medical devices" as such devices are defined by the Jun. 20, 1990 directive 90/385/CEE of the Council of the European Communities, and more particularly to pacemaker, defibrillator and/or cardiovertor devices able to deliver to the heart low energy pulses for the treatment of heartbeat rate disorders. The invention more particularly relates to the adjustment of the amplitude (the voltage level) of the stimulation pulses delivered over time.

BACKGROUND OF THE INVENTION

The ventricular stimulation level or amplitude is typically a value ranging between 1.5 and 5.0 V (±10%), adjustable in step increments of 0.25 V. This amplitude must be sufficiently high to cause the depolarization of the myocardial cavity; it is necessary, however, to avoid values that are too high in order to spare the lifespan of the battery, because the stimulation energy applied to the myocardium, and therefore the corresponding energy consumption of the device, is proportional to the square of the amplitude (and also to the duration) of the pulse.

Also, the amplitude needed to cause the depolarization is a value that can vary over time. Therefore, it is desirable to be able to reevaluate at regular intervals the stimulation amplitude level needed by operating a test of the threshold of effectiveness of the stimulation, called "capture test." The stimulation pulse amplitude is then adjusted on the basis of the capture threshold thus measured, typically at a level that is equal to twice the value of the measured threshold, subject to a minimum (typically 1.5 V) and a maximum (typically 5.0 V) amplitude limit.

The patent publication WO-A-93/02741 and its corresponding U.S. Pat. No. 5,411,533 (both assigned to Ela Medical, the assignee hereof) describe an algorithm for automatically testing the ventricular capture threshold. This algorithm is used in commercial pacemaker products sold under the Talent™ brand, available from Ela Médical, Montrouge, France.

A clinical follow-up of patients equipped with this Talent™ pacemaker device has revealed that, in certain cases, the automatic threshold test algorithm sees its effectiveness reduced because of anomalies occurring at the time of the test. These anomalies may result in an overvaluation of the capture threshold value as compared to the real threshold of the patient. Because any reevaluation of the stimulation amplitude is usually operated every six hours or so, such an excessive level is maintained for at least six hours and, although it is not in itself dangerous, constitutes a source of overconsumption of energy and thus a reduction of the lifespan of the implant.

The aforementioned algorithm for the automatic determination of the capture threshold comprises two specific phases, namely: (1) a preliminary calibration phase, to remove the effect of the polarization of the probe at the heart/electrode interface by determining a reference value; and (2) a measurement phase of the threshold of effectiveness, compared to the reference value previously obtained. As it is easily appreciated, the accuracy of the adjustment is conditioned by the accuracy and the absence of error of the preliminary calibration. The mechanism of a possible calibration error is as follows. The calibration phase comprises at least two measurements of the evoked potential (i.e., a potential of a depolarization consecutive to (i.e., following) a preceding stimulation pulse) for pulses with different amplitudes, for example, pulses of 2 volts and 4 volts. The calibration is regarded as effective if the amplitude of the evoked potential after the calibration stimulation at 2 volts is greater than a certain percentage (typically 25%) of the evoked potential measured with a 4 volt amplitude pulse. But this criterion can be verified for a reason other than an effective capture, which can occur in two circumstances: (1) a very large polarization at the heart/electrode interface, and/or (2) a fusion, i.e., a stimulation intervening in a concomitant way to a spontaneous QRS event occurring at the time of the capture test.

Indeed, the test with 4 volts is always effective (except in the event of a displacement of the probe, but this is an extreme case) and the device will thus measure an evoked potential. On the other hand, the test with 2 volts is ineffective (absence of capture), but the device nevertheless measures a potential which, in fact, is either an elevated polarization potential or a depolarization potential resulting from a fusion that deludes the system and thus results in an erroneous reference.

In the subsequent measurement phase of the capture threshold, the device will systematically measure, for each cycle, the same evoked potential value in spite of the progressive reduction of the stimulation amplitude. Indeed, this measured evoked potential will in fact be only the polarization potential, or the spontaneous depolarization potential resulting from a fusion, in principle always 75% higher than the reference value, and producing an erroneous conclusion of an effective stimulation at each cycle.

U.S. Pat. No. 5,855,594 refers to a method for the determination of the presence of a high voltage of polarization of the electrodes. During a test of capture verification, the device emits pulses with a very low energy below the cardiac capture threshold. The detection of a signal during such stimulations is the sign of a large polarization at the level of the electrodes. However this U.S. patent does not recognize or consider the problem of fusion.

OBJECTS AND SUMMARY OF THE INVENTION

It is, therefore, an object of the present invention to propose a device able to invalidate the calibration and/or the readjustment of the stimulation level in the event of a detection of a positive case of fusion.

To this end, the present invention proposes an active implantable medical device, in particular a pacemaker, defibrillator or cardiovertor, of the general type disclosed in the U.S. Pat. No. 5,855,594 mentioned above, i.e., including stimulation means able to deliver to the heart pulses presenting a predetermined amplitude and duration, and means for adjusting the amplitude of the stimulation pulses, comprising calibrating means, means for delivering a stimulation pulse at null (zero) or at a primarily null voltage (i.e., an effectively null voltage), and means for automatically measuring the ventricular capture threshold, including means for detecting a presence or an absence of a capture consecutive to a stimulation.

According to the invention, the device further includes means for detecting a fusion situation, and means to invalidate the aforementioned adjustment of the stimulation pulses in the event of a detected fusion, these means operating by the delivery of a stimulation pulse at an effectively null voltage, and being able to determine the presence of a fusion in the event of detection of a capture in response to a stimulation at an effectively null voltage.

More particularly, when the means for detecting a fusion situation detects a capture in response to a stimulation at null voltage, these means control the reiteration of the calibrating means, advantageously with a preliminary reduction of the escape interval and/or the atrioventricular delay.

In the alternative or in addition, the means for detecting a fusion situation comprises means able to: (1) deliver a sequence of stimulation pulses at various decreasing successive levels of decreasing voltage and to detect each time the presence or the loss of capture, the stimulation amplitude being adjusted according to the pulse level that produced the loss of the capture, and (2) after application of the last pulse producing a correlative capture, or of the last pulse of the sequence, to apply a pulse at null voltage and validate the adjustment of the threshold amplitude level only when the amplitude of the evoked potential for a stimulation at effectively null voltage is lower than the evoked potential after the aforementioned last stimulation producing a correlative capture.

In all cases, the device very advantageously delivers a counter-stimulation after each delivery of a stimulation at effectively null voltage.

BRIEF DESCRIPTION OF THE DRAWINGS

Further features, characteristics, and advantages of the present invention will appear to a person of ordinary skill in the art in view of the following description of a preferred embodiment of the invention, made with reference to the drawings annexed, in which:

FIG. 1 is a graph showing the evoked potential according to the stimulation pulse amplitude, with the reference and linear regression line (slope) of the capture threshold measurement; and FIG. 2 is a flow chart of a process for detecting the capture threshold in accordance with a preferred embodiment of the invention.

DETAILED DESCRIPTION OF THE INVENTION

The stages of calibration and measurement (or test) are in a preferred embodiment identical to those operated in the known devices, for example, in the manner described in the above mentioned WO-A-93/02741 and U.S. Pat. No. 5,411,533 (which patent is incorporated herein by reference in its entirety), the invention not modifying the way in which either of these two stages is realized. More particularly, as noted above, the algorithm for the automatic determination of the capture threshold comprises two specific phases, namely a preliminary calibration phase to determine a reference value, followed by a threshold search phase, to measure the threshold of effectiveness in comparison to the reference value obtained beforehand.

For the calibration phase, the device measures the evoked potential (or, more precisely, an average of several evoked potential values) for pulses of different amplitudes, for example, at 2 volts and 4 volts.

FIG. 1 represents the evoked potentials Pot2 for a stimulation amplitude of 2 volts, and Pot4 for a stimulation amplitude of 4 volts. The algorithm then determines the linear regression line as a slope between these two values and the ordinate in the beginning, or y-intercept (crossing) b of this line.

The threshold of effectiveness of the capture is then fixed at a value that is a function of this intercept, for example, 75% of the intercept value b (because the intercept overestimates in fact the real polarization value), which constitutes the reference value to which the capture threshold measurement will be compared.

The following stage then concerns determining the crossing of the capture threshold so as to adjust the stimulation pulse amplitude level relative to the "capture threshold," i.e., the minimal stimulation amplitude level allowing the capture. This adjustment is obtained by a progressive, controlled reduction of the level of the amplitude over several successive cycles, the detection of the disappearance of the capture, and then the re-establishment of the amplitude on a level slightly higher than the threshold corresponding to the disappearance.

The test provides three possible results:

1) A "FAILURE" indicator meaning that, because of aberrant results with the calibration, the test cannot provide any meaningful value. The value of the stimulation amplitude is then fixed automatically to the maximum value of 5.0 V for the following period until the next reevaluation of the threshold, e.g., six hours. It should be understood that the six hour period is a preferred duration used in this exemplary embodiment, and a greater or lessor period may be used as a matter of design choice.

2) A "SEARCH" indicator meaning that the algorithm could not be held correctly. In the case that the conditions for launching the test are not fulfilled during the six preceding hours (for example, because of a rhythm that is too fast or the presence of atrial extrasystoles), the stimulation amplitude is forced to have the maximum value of 5.0 V while waiting to launch the test again. If this situation continues during the next six hours, then the algorithm produces the "SEARCH" indicator which is recorded in the statistics file of device.

3) An "OK" indicator with an associated measurement value corresponding to the last threshold with an effective capture that was found by the algorithm. This is the value that will be memorized by the device and used to define the ventricular stimulation amplitude for the next six hours.

The present invention is based on the inventor's observation that, after a calibration stage regarded as effective, although the algorithm cannot determine with certainty whether or not there was capture, it is certain that, if one delivers a stimulation with an amplitude of zero volt, there will not be capture. The invention thus proposes to deliver a stimulation pulse at zero volts during a cycle, and to analyze the amplitude of the corresponding evoked potential, thereby to validate or invalidate a calibration.

In a first embodiment, after the calibration phase and before beginning the threshold measurement phase with the delivery of pulses having successively decreasing amplitudes, the algorithm starts a preliminary stimulation, on one cycle, with an amplitude of zero volts. If the evoked potential is higher than the reference given by the calibration stage, then the calibration is regarded as invalid, and it should either be started again with the same conditions, or started again in a manner better designed to ensure capture by significantly shortening the escape interval (EI) and/or the atrio-ventricular delay (AVD), to avoid being in conflict with a spontaneous conduction, and to prevent the occurrence of a fusion situation.

Another embodiment concerns carrying out the calibration and then the threshold test in the traditional way, with successive pulses of decreasing amplitudes and, after the first ineffective stimulus (or the last stimulus of the series, of a minimal amplitude 0.5 Volt), delivering a stimulus at zero volts during one cycle. The amplitude of the evoked potential after this last stimulus is then compared with that of the last effective pulse: if the difference is not significant (for example, less than 50%), then the test is invalidated and the measurement, including the calibration, must be repeated.

In all cases, for safety reasons, a counter-stimulation pulse is preferably delivered after each measurement during a cycle with a zero volt amplitude stimulation pulse.

The two manners of proceeding described above can be realized alternatively or jointly by the algorithm, as desired in the particular circumstances.

Referring to FIG. 2, a detailed example of an algorithm of a preferred embodiment of the invention is illustrated. After a first initial calibration (stage 10), a test is carried out in which an Amplitude A of zero volts (stage 12), i.e., a stimulation pulse with an amplitude of zero volts is delivered by the device. The evoked potential Pot0 in response to the stimulation with zero volts is then measured and compared with the evoked potential Pot2 in response to a stimulation at 2 volts at the time of the calibration phase (stage 14). If Pot0 is much lower than Pot2 (stage 14), the calibration is validated and the threshold test (stage 16) can then start, by delivery of successive pulses with an amplitude level decreasing over several cycles.

Once the disappearance of the capture is detected (stage 18), a new test with zero volt is operated (stage 20). If the evoked potential corresponding to Pot0 is much lower than the evoked potential of the last effective pulse of the threshold test, and if it is lower than the reference value (stage 22), then the stimulation level amplitude A is reprogrammed according to the new capture threshold value (stage 24); in the contrary case, the stimulation amplitude A is forced, for safety reasons, to its maximum level of 5.0 volts, and the readjustment of the amplitude level will be deferred to a later time, for example, six hours later (stage 26). It also is possible to rerun the test at stage 28.

If, at the stage 14, Pot0 is not notably lower than Pot2, assuming a possible fusion situation, the stimulation parameters are modified (stage 28). For example, the escape interval (EI) is decreased, for example, by 150 ms and the atrio-ventricular delay (AVD) is decreased, for example, by 31 ms. Before carrying out this reduction, the algorithm ensures that value AVD-31 ms is higher or equal to a minimal limit set for the apparatus, for example, 78 ms (test not shown). If it is not possible to decrease the programmed AVD by 31 ms, then the algorithm passes directly to stage 46.

A new test with zero volt is then carried out (stage 30). If the evoked potential corresponding to Pot 0 is not notably lower than the last effective measured value of Pot2, or is not lower than the reference value (stage 32), then the stimulation amplitude is forced, for safety reasons, to its maximum level of 5.0 volts, and the readjustment of the amplitude level will be deferred to a later time, for example, six hours later (stage 34). In the contrary case, the calibration is validated and the threshold test is carried out with the modified stimulation parameters (stage 36).

Once the disappearance of the capture is detected (stage 38), a new test with a zero volt amplitude is operated (stage 40). If the evoked potential corresponding to Pot0 is much lower than the evoked potential of the last effective pulse of the threshold test, and if it is lower than the reference value (stage 42), then amplitude A of the stimulation level is reprogrammed according to the new capture threshold value (stage 44); in the contrary case, the stimulation amplitude is forced, for safety reasons, to its maximum level of 5.0 volts, and the readjustment of the amplitude level will be deferred to a later time, for example, six hours later (stage 46).

It should be understood that the present invention is preferably implemented in software of a microprocessor controlled implantable medical device. Suitable devices include, but are not limited to the aforementioned Talent™ pacing device. Advantageously, the present invention can be downloaded to an already implanted device by an external programmer, in a conventional manner, as software instructions to modify the operation of the already implanted device, for such devices that are able to receive software instructions and to modify its operation in response thereto.

One skilled in the art will appreciate that the present invention can be implemented by embodiments other that the particular embodiments disclosed, which are presented for purposes of illustration, and not of limitation.

I claim:

1. An active implantable medical device, in particular a pacemaker, defibrillator or cardiovertor, having:

stimulating means for delivering to a heart stimulation pulses presenting a predetermined amplitude and a duration;

means for adjusting the amplitude of said stimulation pulses, including:
      means for calibrating the stimulation pulse,
      means for delivering the stimulation pulse at effectively a null voltage, and
      means for measuring automatically a ventricular capture threshold, including means for detecting a presence or an absence of a capture consecutive to the stimulation pulse;

means for determining the presence of a fusion situation in response to the detection of the presence of a capture in response to the stimulation pulse delivered at effectively null voltage; and means for invalidating the adjustment of the stimulation pulse's amplitude in response to the determination of the presence of a fusion situation.

2. The device of claim 1, further comprising a means for controlling a reiteration of the calibrating means.

3. The device of claim 2, further comprising a means for shortening the time of at least one of an escape interval or atrio-ventricular delay prior to the reiteration of the calibrating means.

4. The device of claim 1, wherein the fusion situation determining means further comprises:

means for delivering a sequence of stimulation pulses at various successively decreasing voltage levels and for detecting a presence or a loss of capture in response to each said pulse, wherein the stimulation amplitude is adjusted according to the pulse level associated with a detected loss of capture; and means, operable after delivering the last pulse associated with a detected capture, or of the last pulse of the sequence, for applying the stimulation pulse at effectively null voltage and validating the adjustment of the amplitude level in response to the amplitude of the evoked potential responsive to said stimulation at effectively null voltage being lower than the evoked potential responsive to said last stimulation associated with a detected capture.

5. The device of claim 1, further comprising means for delivering a counter-stimulation subsequent to a delivery of the stimulation at effectively null voltage.

* * * * *